(12) United States Patent
Kobayashi

(10) Patent No.: US 7,478,947 B2
(45) Date of Patent: Jan. 20, 2009

(54) RADIATION IMAGING APPARATUS AND TABLE THEREFOR

(75) Inventor: Masaaki Kobayashi, Shimotsuga-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 179 days.

(21) Appl. No.: 11/549,894

(22) Filed: Oct. 16, 2006

(65) Prior Publication Data

US 2007/0086577 A1    Apr. 19, 2007

(30) Foreign Application Priority Data

Oct. 17, 2005    (JP)    ............................. 2005-301275

(51) Int. Cl.
G03B 42/02    (2006.01)

(52) U.S. Cl. ...................... 378/181; 378/167; 378/177; 378/189

(58) Field of Classification Search ................... 378/91, 378/115, 116, 117, 177, 189, 195, 196, 209, 378/25, 26, 181, 197, 167; 5/601
See application file for complete search history.

(56) References Cited

U.S. PATENT DOCUMENTS

| 3,743,843 | A | * | 7/1973 | Reser et al. .................... 378/27 |
| 3,904,531 | A | * | 9/1975 | Barrett et al. ................ 378/181 |
| 4,095,110 | A | * | 6/1978 | Bunch .......................... 378/26 |
| 4,450,575 | A | * | 5/1984 | Mueller ........................ 378/26 |
| 5,020,089 | A | * | 5/1991 | Cramer et al. .............. 378/196 |
| 5,023,899 | A | * | 6/1991 | Ohlson ........................ 378/196 |
| 5,177,778 | A | * | 1/1993 | Tsurumaki et al. .......... 378/117 |
| 5,422,928 | A | * | 6/1995 | Payne .......................... 378/177 |
| 5,485,502 | A | * | 1/1996 | Hinton et al. ................ 378/117 |
| 5,572,567 | A | * | 11/1996 | Khutoryansky et al. ..... 378/197 |
| 5,703,925 | A | * | 12/1997 | Wright ........................ 378/181 |
| 5,751,788 | A | * | 5/1998 | Khutoryansky et al. ..... 378/197 |
| 5,764,724 | A | * | 6/1998 | Ohlson ....................... 378/177 |
| 5,878,112 | A | * | 3/1999 | Koertge ...................... 378/209 |
| 6,045,262 | A | * | 4/2000 | Igeta et al. .................. 378/209 |
| 6,075,256 | A |   | 6/2000 | Kaifu et al. |
| 6,302,580 | B1 | * | 10/2001 | Dwyer et al. ............... 378/197 |
| 6,341,156 | B1 | * | 1/2002 | Baetz et al. ................ 378/98.8 |
| 6,435,713 | B1 | * | 8/2002 | Iizuka ........................ 378/195 |
| 6,463,121 | B1 | * | 10/2002 | Milnes ........................ 378/62 |
| 6,508,586 | B2 | * | 1/2003 | Oota .......................... 378/196 |
| 6,934,361 | B2 |   | 8/2005 | Ohkoda |
| 7,130,378 | B2 | * | 10/2006 | Akutsu et al. ............... 378/117 |

FOREIGN PATENT DOCUMENTS

JP    08-116044    5/1996
JP    2003-038472    2/2003

* cited by examiner

*Primary Examiner*—Allen C. Ho
(74) *Attorney, Agent, or Firm*—Canon USA Inc. IP Division

(57) ABSTRACT

A radiation imaging apparatus including a tabletop onto which a patient lays down, a radiation imaging unit positioned below the tabletop and configured to detect radiation that transmits through the patient, a widthwise moving member supporting the tabletop and configured to move the tabletop in a widthwise direction, a moving mechanism unit including a lengthwise moving mechanism configured to move the tabletop in a lengthwise direction, the moving mechanism unit supporting the widthwise moving member and supporting the radiation imaging unit so as to be movable in the lengthwise direction, and a base unit supporting the moving mechanism unit.

4 Claims, 9 Drawing Sheets

RADIATION IMAGING APPARATUS AND TABLE THEREFOR

BACKGROUND OF THE INVENTION

1. Field of the Invention

The present invention relates to a radiation imaging apparatus that projects radiation such as X-ray to a patient (subject) who is laying down on a tabletop of a table and a bed, and photographs with the radiation that transmits through the patient using a radiation imaging unit disposed below the tabletop, and also relates to a table for the radiation imaging apparatus.

2. Description of the Related Art

Conventionally, radiation imaging apparatuses are used in various fields such as in nondestructive inspection of a material. In this kind of radiation imaging apparatus, a so-called radiography is utilized in which an intensifying screen and a radiographic film are brought into close contact with each other. In the radiation imaging apparatus, when the radiation that transmits through the patient is incident on the intensifying screen, a phosphor included in the intensifying screen absorbs energy from the radiation and shows a fluorescence. The radiographic film is exposed to the fluorescence so that a radiological image is then recorded as a visible image.

In recent years, an image recording and reproducing apparatus equipped with a radiation detection device including a stimulable phosphor is devised. In the image recording and reproducing apparatus, when the radiation transmits through the patient and is incident on the stimulable phosphor, the stimulable phosphor stores apart of the radiation energy. When light such as visible light is radiated onto the storage phosphor, in the image recording and reproducing apparatus, the stimulable phosphor shows gleaming luminescence in accordance with the stored energy. That is, the stimulable phosphor stores radiation image information of the patient, and a scanning unit scans the storage phosphor with an excitation light such as a laser beam. Then, a signal reading unit photoelectrically reads the gleaming phosphorescence, and a recording material such as a photosensitive material or a display unit such as a CRT, records or displays the read information as the visible image.

Japanese Patent Application Laid-Open No. 08-116044 (corresponding to U.S. Pat. No. 6,075,256) discusses a radiation detection device that directly outputs digital data of the radiation in real time. The radiation digital detection device has a laminated configuration of a scintillator and a photoelectric conversion device. The scintillator converts the radiation into visible light and the photoelectric conversion device photoelectrically converts the visible light In the photoelectric conversion device, photoelectric conversion elements interposed between a transparent conducting material and an amorphous semiconductor film that includes a conducting material are arranged in a matrix on a substrate of silica glass.

Because the radiation detection device is a flat panel having a thickness of several millimeters, the radiation imaging unit that uses the radiation detection device can be easily reduced in thickness and weight. In addition, the radiation imaging unit is capable of directly obtaining a digital image without using a consumable material such as a film and a stimulable phosphor sheet. Accordingly, conventional work of mounting a cassette that stores the film or the stimulable phosphor sheet on the radiation imaging unit, is not necessary. Further, to take out the cassette in order to develop the film or the stimulable phosphor sheet after the imaging, is not necessary. Thus, a radiologist is free from complicated work.

FIG. 10 is a diagram that illustrates a conventional Bucky table that can be used to simply photograph a patient's extremities, head, and abdominal parts. In the Bucky table, a base 1 supports a tabletop 3 that allows the patient to lie down thereon via a supporting member 2. A radiation imaging unit 4 is disposed on the base 1 that is provided on an underside of the tabletop 3. In a space within the radiation imaging unit 4, the radiation detection device described above is installed. In photographing the patient laying down on the tabletop 3 on his back or on his belly, the patient is exposed to the X-ray irradiated by an X-ray tube 5 that is disposed above the patient, and the X-ray that transmits through the patient is received by the radiation imaging unit 4 so as to form the image thereof.

The radiologist needs to align a position of a part of the patient to be photographed and an image-receiving region of the radiation imaging unit 4. In order to implement the positional alignment, the Bucky imaging table includes roughly two units. One is a unit that moves the tabletop 3 in a horizontal direction so as to align the part of the patient to be photographed with the position of the image-receiving region of the radiation imaging unit 4. The other is a unit that moves the radiation imaging unit 4 so as to align the image-receiving region of the radiation imaging unit 4 with the position of the part of the patient to be photographed.

The tabletop 3 is capable of moving on the supporting member 2 for a distance L1. The radiation imaging unit 4 is capable of moving on the base 1 for a distance L2. The radiologist performs the photographing by selectively using the moving units in accordance with the circumstance and a state of the patient. However, when the radiation imaging unit 4 is moved to a leftmost position and the tabletop 3 is moved to a rightmost position at the same time, in the Bucky table as shown in FIG. 10, a left most portion of a photographing scope cannot be positioned to a close proximity of a leftmost position of the tabletop 3. That is, in photographing an extremity of the patient who is lying down, it is easy to photograph a part of the patient ranging from a cervical spine to a thigh. However, it is difficult to cover the entire extremity of the patient including the head and the leg. In addition, in the method by which both the tabletop 3 and the radiation imaging unit 4 are moved, working performance is low, and an effective photographing operation cannot be performed.

Japanese Patent Application Laid-Open No. 2003-38472 (corresponding to U.S. Pat. No. 6,934,361) discusses the radiation imaging apparatus that is capable of freely disposing the units so as to effectively operate the photographing operation. In the radiation imaging apparatus, a supporting member that supports a radiation image detection device at a position below a tabletop unit is provided to the tabletop. Thus, the radiation image detection device can be disposed and moved to a desired position over a whole part of an underside of the tabletop.

The radiation imaging apparatus disclosed in Japanese Patent Application Laid-Open No. 2003-38472 includes a detection unit that detects a first moving vector that indicates the movement of the tabletop on the base. In addition, the radiation imaging apparatus includes a moving unit that moves the radiation image detecting device in relation to the tabletop unit so that a second moving vector that indicates the movement of the radiation image detecting device in relation to the tabletop, is −1 times of the first moving vector. Thus, the photographing operation of a wide range of the patient can readily be performed.

In the conventional table, the tabletop 3 is very often slid in a widthwise direction in aligning the portion of the patient to be photographed to the position of the radiation imaging unit.

FIG. 11A and FIG. 11B are diagrams that describe a positional relationship between the tabletop 3 and the radiation imaging unit 4 seen from a side of a shorter side of the tabletop 3 shown in FIG. 10, that is, from a direction of an arrow A shown in FIG. 10. Here, the tabletop 3 is supported by a tabletop frame 6. FIG. 11A shows a state in which a center of the tabletop 3 and a center of the radiation imaging unit 4 in the widthwise direction match with each other, and FIG. 11B shows a state in which the tabletop 3 is slid in a widthwise direction.

In an ordinary case, the width of the tabletop 3 in the widthwise direction is approximately 8000 mm, and the width of the radiation imaging unit 4 is approximately 5500 mm, which enables photographing by 4300 mm using 14×17 inch size film. Here, a movement amount of the tabletop 3 in the widthwise direction should be about ±150 mm. Thus, in an ordinary floating table, when the tabletop 3 is moved at a maximum, the tabletop frame 6 moves for a distance L3 so as to be positioned above the radiation imaging unit 4. In this case, the disposition of the tabletop frame 6 is as shown in FIG. 11B.

FIG. 11C is a diagram that illustrates the positional relationship in the radiation imaging apparatus that Japanese Patent Application Laid-Open No. 2003-38472 discusses. Referring to FIG. 1C, the radiation imaging unit 4 is supported by a rail 7 provided in the tabletop frame 6. Thus, the radiation imaging unit 4 can move between the rails 7.

Because of the existence of the rail 7, the tabletop 3 cannot move out of the radiation imaging unit 4. Thus, a movement amount L4 of the radiation imaging unit 4 is smaller compared to the movement amount L3 as shown in FIG. 11B. Therefore, in order to secure a sufficient movement amount, the distance between two rails 7 needs to be lengthened.

That is, as a countermeasure, the width of the tabletop 3 can be broadened. However, when the width of the tabletop 3 is broadened, a space for installation can increase. Alternatively, as a countermeasure, the radiation imaging unit 4 can go under the rail 7. However, with this configuration, the distance between the radiation imaging unit 4 and the tabletop 3 becomes longer. As described above, in the conventional examples, enlargement of the movement amount of the tabletop 3 in the widthwise direction can be restricted.

In the conventional table, when the radiation imaging unit 4 is moved in the widthwise direction, the radiologist needs to align the position of the X-ray tube 5 precisely with the center of the radiation imaging unit 4. This is because if there is a difference between a convergence position of grids used for eliminating a scattered radiation and the position of the X-ray tube 5 in the horizontal direction, an effective transmissive X-ray is cut off. In the conventional example, occurrence of the difference of the positions is prevented by adding a mechanism which moves the X-ray tube 5 according to the movement of the radiation imaging unit 4. However, while there is the X-ray tube 5 that can move according to the movement of the radiation imaging unit 4 in a lengthwise direction in a tomography etc., few X-ray tubes 5 can move according to the movement of the radiation imaging unit 4 in the widthwise direction.

In addition, as shown in FIG. 10, the radiation imaging unit 4 essentially covers the whole part of a photographing object without moving in the widthwise direction, if an image-receiving scope is enlarged. Thus, a mechanism for moving the radiation imaging unit 4 in the widthwise direction is not required. However, when the radiation imaging unit 4 is supported by the tabletop 3, in terms of structure, a mechanism for moving the radiation imaging unit 4 in the widthwise direction is necessary. For example, the tabletop 3 can be moved instead of moving the radiation imaging unit 4 so as to align the radiation imaging unit 4 with the position of the photographing portions of the patient. However, in this method, when the tabletop 3 is moved in the widthwise direction, the radiation imaging unit 4 has to be moved back to an original position in the same movement amount as the tabletop 3.

In addition, in the conventional table, when the radiation imaging unit 4 and a supporting member that supports the radiation imaging unit 4 are provided in the moving tabletop 3, a gross mass of the tabletop 3 and an inertial force of the tabletop 3 increase. Accordingly, a force required for moving at the time of operation by the radiologist, and a sway of the imaging table at the time of stopping the moving operation increase, and thus operability can deteriorate. Especially, the sway that occurs at the time of stopping the movement in the widthwise direction, causes also the body of the patient to sway so that the patient feels unnecessary pain.

As described above, the conventional table is good in the operability of the tabletop 3 in the lengthwise direction, but there is a defect with respect to the operability of the tabletop 3 in the widthwise direction.

In addition, in moving the tabletop 3 on a horizontal plane, a sufficient space is necessary around the apparatus in accordance with the movement amount of the tabletop 3. However, in actual use, instruments such as a drip infusion stand and a monitoring device for the patient are placed around the table. Accordingly, the movement range of the tabletop 3 in the widthwise direction can be restricted. In this case, the radiologist is required to deliberately perform the operation while confirming the surrounding state, and thus the operability deteriorates.

SUMMARY OF THE INVENTION

The present invention is directed to a radiation imaging apparatus and a table for the apparatus that are capable of performing an effective photographing operation by moving a tabletop in a widthwise and lengthwise directions.

According to an aspect of the present invention, a radiation imaging apparatus includes a tabletop onto which a patient lays down; a radiation imaging unit positioned below the tabletop and configured to detect radiation that transmits through the patient; a widthwise moving member supporting the table top and configured to move the tabletop in a widthwise direction; a moving mechanism unit including a lengthwise moving mechanism configured to move the tabletop in a lengthwise direction, the moving mechanism unit supporting the widthwise moving member and supporting the radiation imaging unit so as to be movable in the lengthwise direction; and a base unit supporting the moving mechanism unit.

Further features of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE EMBODIMENTS

Exemplary embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
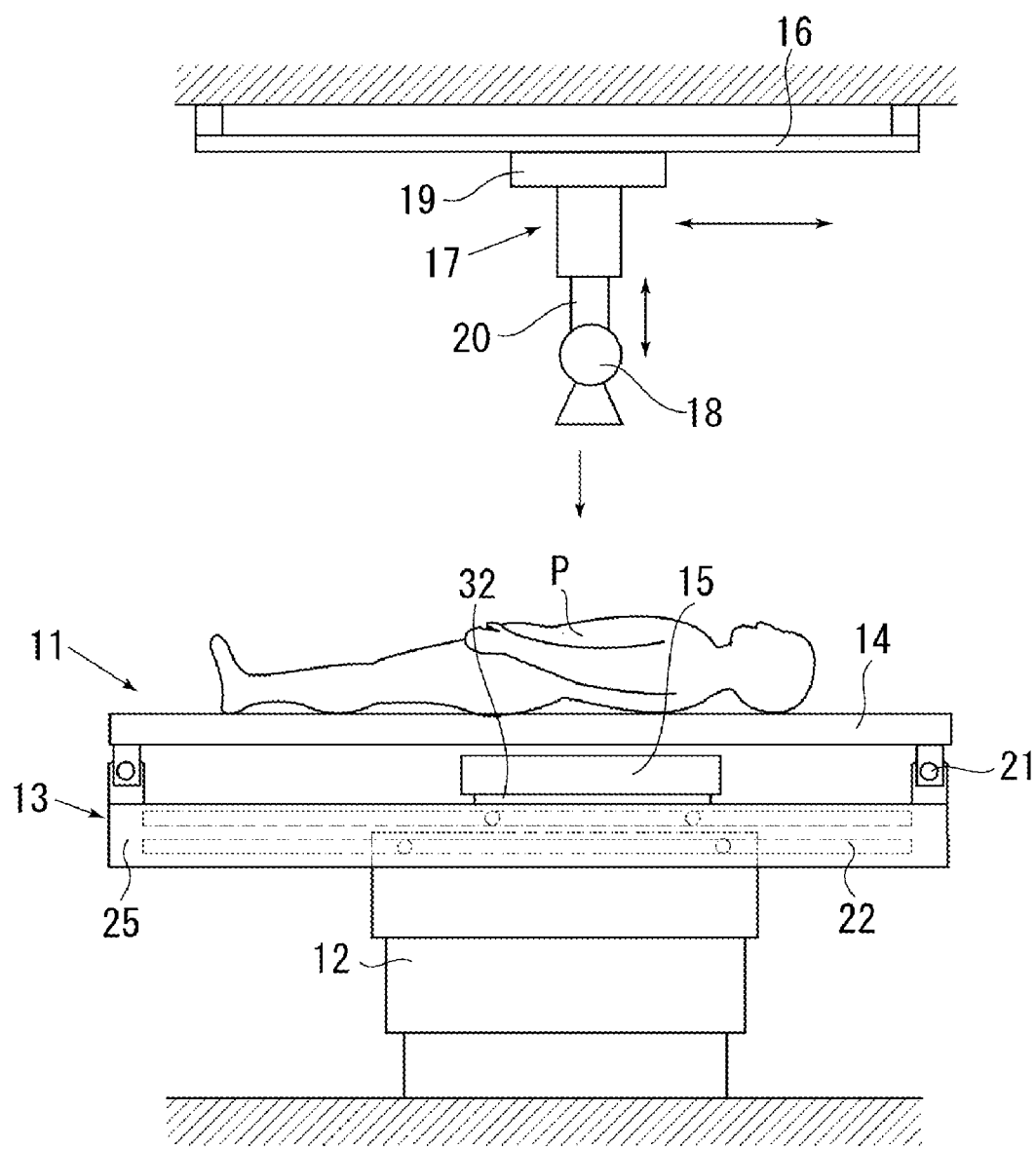
FIG. 1 is a diagram that illustrates a radiation imaging apparatus according to a first embodiment of the present invention seen from a longer side of the radiation imaging apparatus.

FIG. 1 is a diagram that illustrates a configuration of a radiation imaging apparatus according to a first embodiment of the present invention seen from a longer side of a tabletop. A table 11 is fixed onto a floor of an imaging chamber. The table 11 is provided with a tabletop moving mechanism unit 13 via a base unit 12. A tabletop 14 onto which a patient P lays down, can move in a horizontal plane and is placed onto the tabletop moving mechanism unit 13. A radiation imaging unit 15 contains an X-ray image detection device. The X-ray image detection device detects X-rays that is transmitted through the patient P, and is disposed on the tabletop moving mechanism unit 13.

A tube supporting mechanism 17 and an X-ray tube 18 are provided above the table 11. The tube supporting mechanism 17 is suspended via a rail 16 provided to a ceiling of the imaging chamber, and the X-ray tube 18 is installed to a lower portion of the tube supporting mechanism 17. The tube supporting mechanism 17 includes a horizontal movement member 19 and a vertical movement member 20. The tube supporting mechanism 17 can move in a lengthwise direction (along the body length of the patient shown in FIG. 1) of the tabletop 14 and in a widthwise direction (along the body width of the patient in FIG. 1) of the tabletop 14 using the rail 16. The vertical movement member 20 can be lengthened and shortened in a vertical direction.

The tabletop moving mechanism unit 13 includes a widthwise movement mechanism 21 that moves the tabletop 14 in the widthwise direction, and a lengthwise movement mechanism 22 that moves the tabletop 14 in the lengthwise direction. With these mechanisms, the tabletop 14 is capable of moving within a horizontal plane.

The tabletop 14, the widthwise movement mechanism 21, and the lengthwise movement mechanism 22 are disposed on the base unit 12, in an order from top to bottom. The table according to this embodiment differs from a conventional table in which a tabletop, a lengthwise movement mechanism, a widthwise movement mechanism, and a base unit are disposed in an order from top to bottom.

Figure 2:
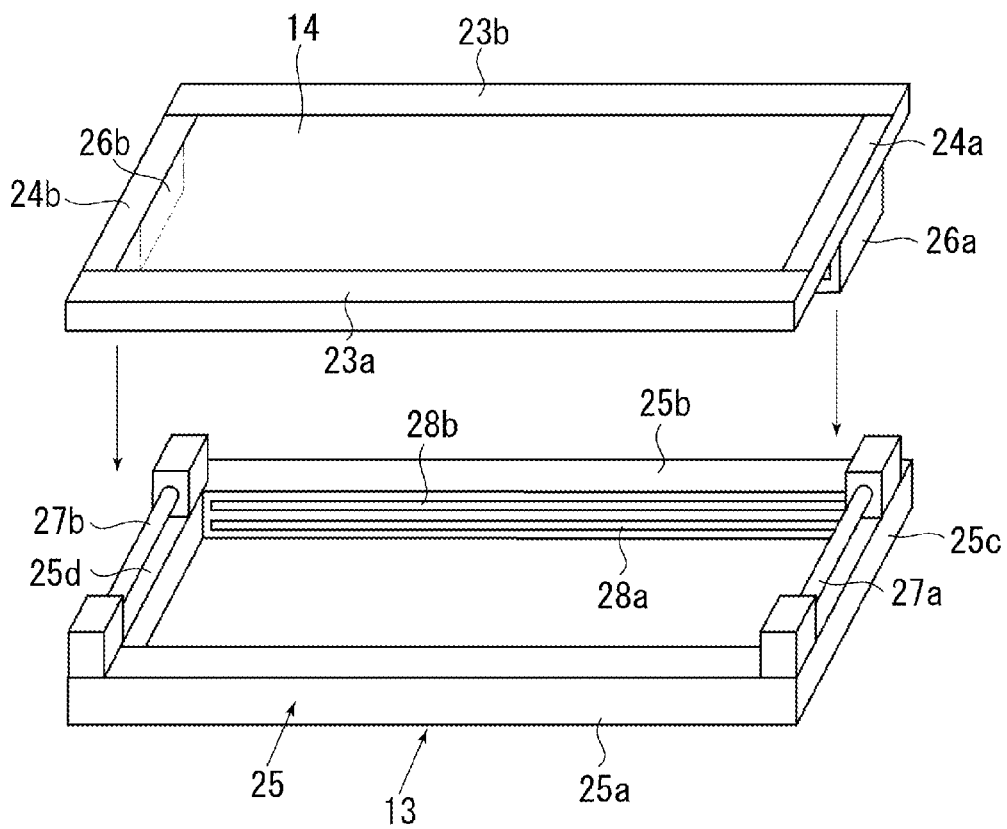
FIG. 2 is a diagram that illustrates a tabletop moving mechanism unit and a tabletop unit according to the first embodiment of the present invention.

FIG. 2 is a diagram that illustrates a configuration of the tabletop moving mechanism unit 13 and the tabletop 14. The tabletop 14 includes a plate material having a high X-ray transmissivity such as an acrylic sheet, a carbon sheet, and a wooden material. The tabletop 14 includes longer side frame members 23a and 23b having a sufficient rigidity, and shorter side frame members 24a and 24b. These members are disposed in a manner surrounding four sides. A frame 25 that supports the tabletop 14 includes frame members 25a through 25d. The frame 25 has a frame shape of approximately the same dimension as the frame members 23a, 23b, 24a, and 24b, and is made of a material having a sufficient rigidity.

The widthwise movement mechanisms 21 are disposed at both ends of the tabletop 14 in the lengthwise direction. The widthwise movement mechanism 21 includes linear motion bearings 26a and 26b provided under the shorter side frame members 24a And 24b, and shafts 27a and 27b provided on the widthwise direction frame members 25c and 25d. The shafts 27a and 27b are inserted into the linear motion bearings 26a and 26b. Sliding movement of the shafts 27a and 27b enables the tabletop 14 to freely move in the widthwise direction.

Figure 3:
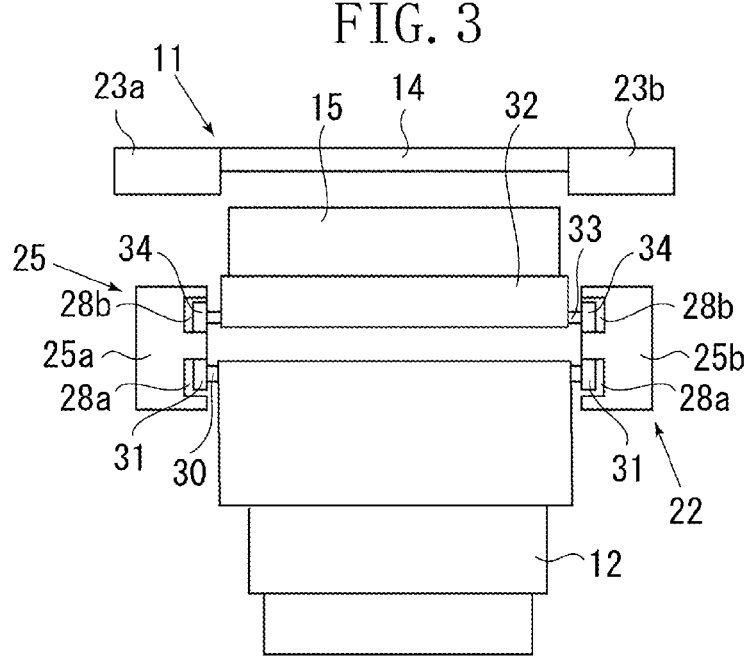
FIG. 3 is a diagram that illustrates the radiation imaging apparatus seen from a shorter side of the radiation imaging apparatus according to the first embodiment of the present invention.
Figure 11A:
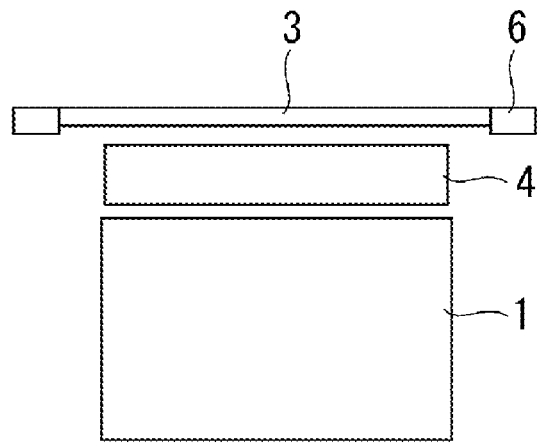
FIG. 11A, FIG. 11B, and FIG. 11C are explanatory diagrams that respectively illustrate a positional relationship between the tabletop and a radiation imaging unit according to the conventional example.
Figure 11B:
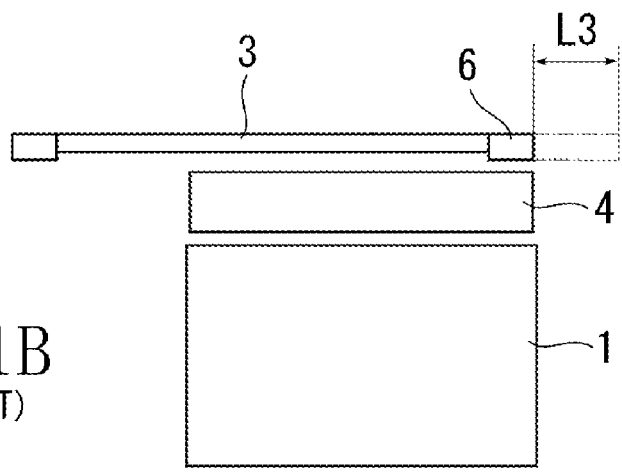
Figure 11C:
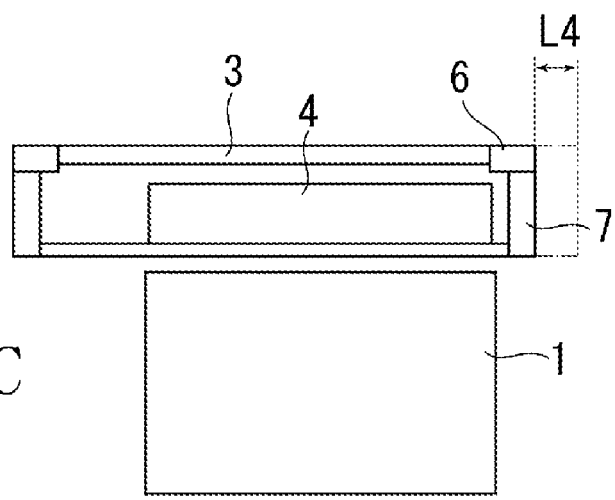

FIG. 3 is a diagram that illustrates a side view of the imaging table 11 as shown in FIG. 11 and seen from the shorter side of the tabletop 14. The lengthwise movement mechanism 22 includes a mechanism that linearly moves the frame 25 in the lengthwise direction in relation to the base unit 12. The lengthwise direction frame members 25a and 25b are disposed in a manner protruding the base unit 12 at both sides. In an inside of the lengthwise direction frame members 25a and 25b, first and second slots 28a and 28b are formed which extend in the lengthwise direction. A roller 31 that is pivotally supported by a shaft 30 attached to the base unit 12, rotates inside the first slot 28a. Thus, the frame 25 and the components above the frame 25, including the tabletop 14, can move in the lengthwise direction in relation to the base unit 12. Using a combination of the lengthwise movement mechanism 22 and the widthwise movement mechanism 21, the tabletop 14 can freely move within the horizontal plane.

On the other hand, the radiation imaging unit 15 is positioned below the tabletop 14. In the inside of the radiation imaging unit 15, an X-ray image detecting device is provided that receives an image of the X-ray which transmits through the patient P. The radiation imaging unit 15 is disposed in a space interposed between the tabletop 14 and the base unit 12 so as to be fixed onto a carriage 32. The carriage 32 is supported so as to be movable in the lengthwise direction in relation to the frame 25.

The carriage 32 is horizontally supported by the second slot 28b of the frame 25, via a shaft 33 and a roller 34. When the roller 34 rotates inside the second slot 28b, the carriage 32 can move in the lengthwise direction along the second slot 28b. The rollers 34 are provided in the carriage 32 at at least three positions, and thus a horizontal attitude of the carriage 32 can be stabilized.

The second slot 28b is provided along almost the entire length of the frame members 25a and 25b, and thus the radiation imaging unit 15 can move along almost the entire length of the tabletop 14.

By moving the tabletop 14 and the radiation imaging unit 15, the radiation imaging unit 15 can be disposed at various positions in relation to the patient P. That is, the photographing operation in any portions can be performed without moving the patient lying on the tabletop 14. Further, the patient P can be easily photographed without lying down on the tabletop 14, in such a manner that the patient P is positioned to the side of the table 11 and the portion to be photographed is positioned on the tabletop 14. Note that in this embodiment, the radiation imaging unit 15 is not moved in the widthwise direction. This is intended to avoid the alignment of the X-ray tube 18 so as to improve operability, and also to simplify the configuration and to cut down the manufacturing cost of the apparatus.

The base unit 12 supports the tabletop moving mechanism unit 13, and contains an ascending and descending mechanism which vertically moves the tabletop 14 in an ascending and descending direction. The ascending and descending mechanism can change a vertical distance from the floor of the imaging chamber. Thus, when the patient P climbs onto the tabletop 14, a height of the tabletop 14 can be lowered down to a position at which the patient P feels less pain. When the patient P is moved onto the tabletop 14 from a stretcher, the height of the tabletop 14 can be adjusted to a height at which a person who looks after the patient can easily work.

Figure 4:
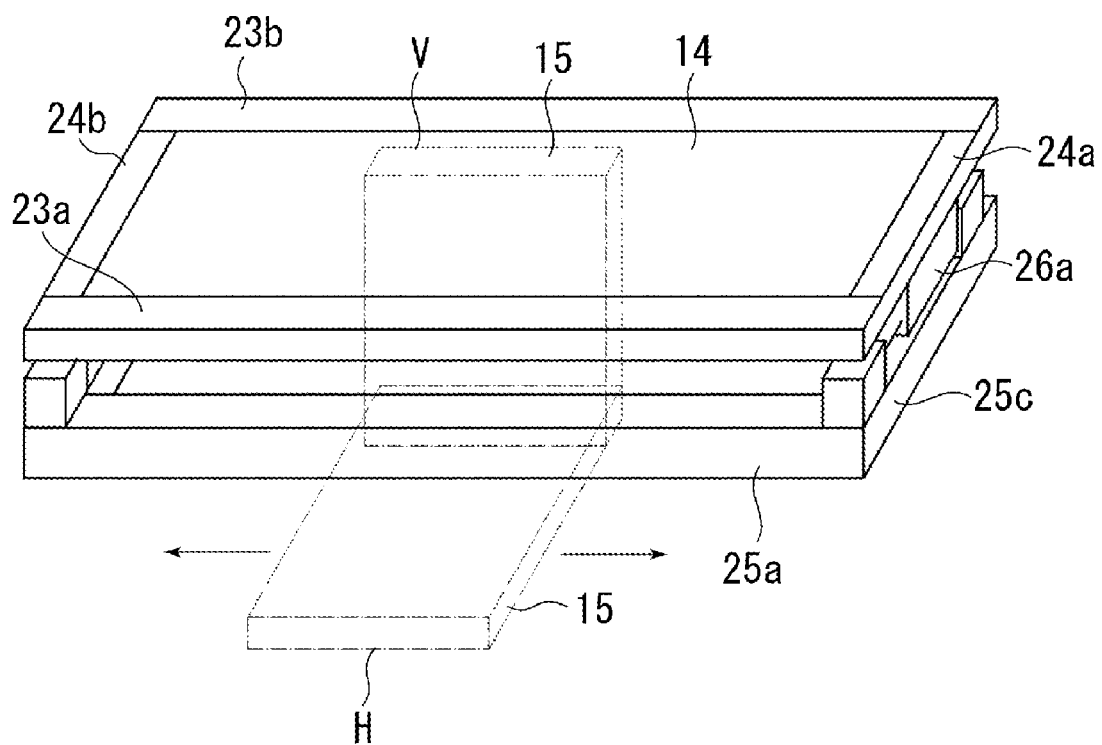
FIG. 4 is an explanatory diagram that illustrates a state in which an attitude of the radiation imaging unit is changed according to the first embodiment of the present invention.

Further, in the imaging apparatus according to this embodiment, no structural unit is provided to a side surface of the radiation imaging unit 15, namely, in the direction of the widthwise movement (i.e., the imaging apparatus is unobstructed at the side surface of the radiation imaging unit). Thus, a mechanism can be added to the carriage 32 by which, for example, the state of the radiation imaging unit 15 can be changed to a state H in which the radiation imaging unit 15 is drawn out to the widthwise direction of the tabletop 14, and to a state V in which the radiation imaging unit 15 is directed in a vertical direction to the side of the tabletop 14 after being drawn out as shown in FIG. 4. In addition, the radiation imaging unit 15 can be moved over an entire portion of the tabletop 14 maintaining these states, and accordingly, the photographing operation can be performed in various forms.

In the photographing operation, grids for eliminating scattered radiation are installed inside the radiation imaging unit 15. In the case where the photographing portion of the patient requires no grids, the work for taking out the grids from the radiation imaging unit 15 can readily be performed in any position. Further, while the radiation imaging unit 15 according to this embodiment contains the X-ray detection device, in the case of the radiation imaging unit that uses a conventional analog cassette, the work for exchanging an unused cassette and a photographed cassette can be performed in any position.

The alignment of the photographing portion of the patient with the image-receiving region of the radiation imaging unit can be performed by moving the tabletop 14 or the radiation imaging unit 15, or by a combination of both. When the tabletop 14 is moved by manual operation, the alignment can be performed in a short length of time while securing the safety of the patient P. Accordingly, the manual operation is widely used. Besides, in the case of moving the radiation imaging unit 15, an electrical control by a motor and the manual operation can be used.

Second Embodiment

Figure 5:
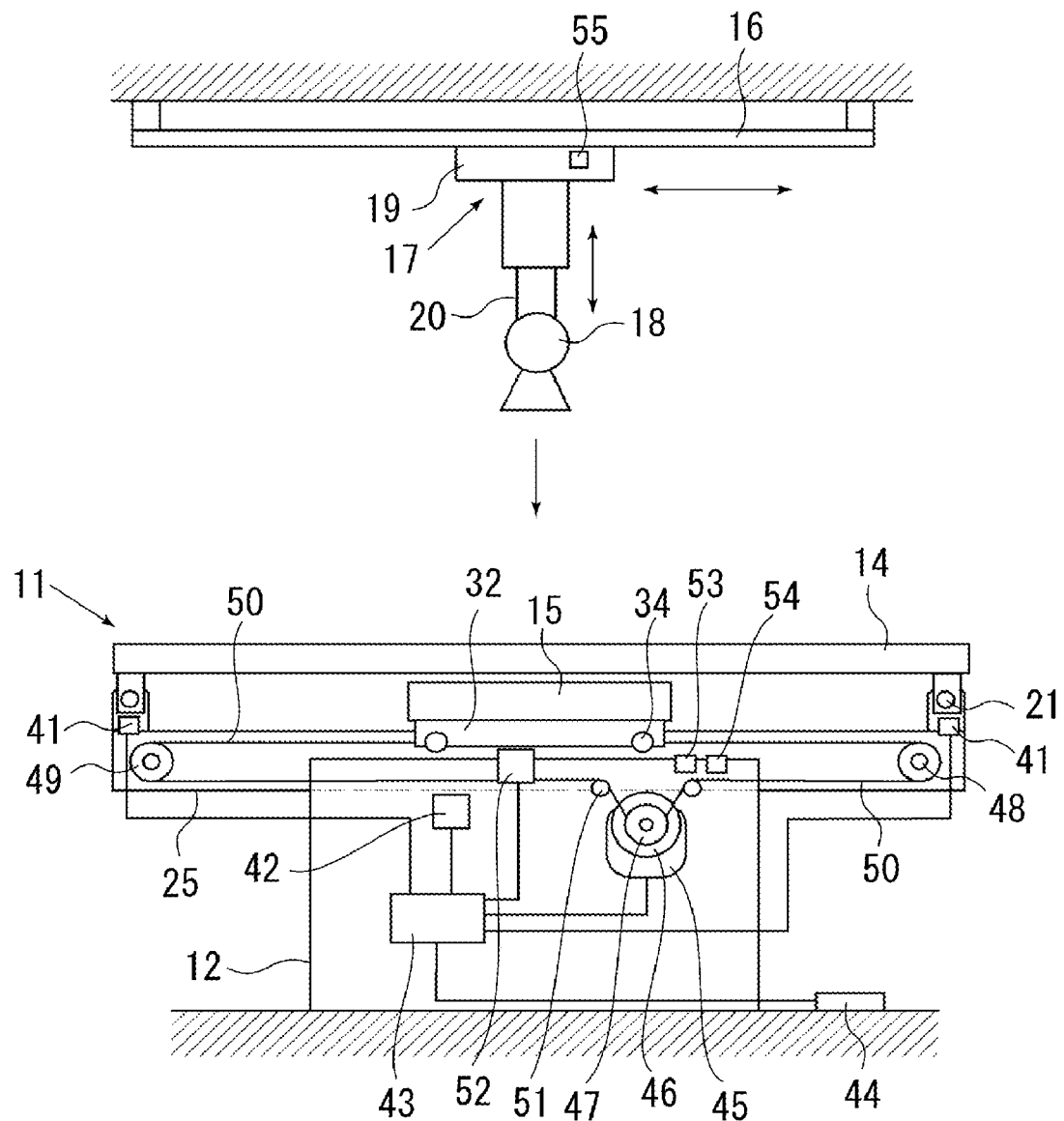
FIG. 5 is a diagram that illustrates the radiation imaging apparatus according to a second embodiment of the present invention.

FIG. 5 is a diagram that illustrates a mechanism for electrically moving the radiation imaging unit 15 which is added as a component necessary for the alignment to the basic configuration of the first embodiment. The same components as the first embodiment are provided with the same numerals and symbols. At both ends of the frame 25, a widthwise locking mechanism 41 that fixes the movement of the tabletop 14 in the widthwise direction is provided. In the same way, the base unit 12 is provided with a lengthwise locking mechanism 42 that fixes the movement of the frame 25 in the lengthwise direction. The locking mechanisms 41 and 42 respectively include an electromagnet, and are capable of inhibiting free movement of the tabletop 14 while the electromagnet fixes the tabletop 14 to the frame 25 by the absorption effect. The operation of the locking is performed by a controller 43, and the releasing operation of the locking is performed by a foot switch 44 provided to the side of the base unit 12 that includes a microswitch.

The base unit 12 includes a drive unit 45 such as a motor. A driving shaft of the drive unit 45 is connected to a driving pulley 47 via a clutch 46. At each end of the frame 25, driven pulleys 48 and 49 are provided. Between the two driven pulleys 48 and 49, a timing belt 50 is wound. A lower portion of the timing belt 50 is given tension by an auxiliary roller 51 inside the base unit 12, and thus the timing belt 50 is disposed so as to be engaged to the driving pulley 47. On the other hand, a part of an upper portion of the timing belt 50 is fixed to the carriage 32 so that the radiation imaging unit 15 moves in the lengthwise direction in accordance with the driving pulley 47.

Inside the base unit 12, an imaging unit locking mechanism 52 is provided that fixes the movement of the radiation imaging unit 15 in the lengthwise direction. The imaging unit locking mechanism 52 is controlled by the controller 43. By absorption-fixing the carriage 32 using the electromagnet as in the case of the locking mechanisms 41 and 42 of the tabletop 14, the controller 43 inhibits the movement of the radiation imaging unit 15. A displacement of the tabletop 14 and the radiation imaging unit 15 in a widthwise direction in relation to the base unit 12 is measured by a position sensor 53 of the tabletop 14 and a position sensor 54 of the radiation imaging unit 15. A measured value is inputted to the controller 43.

With the configuration as described above, in a normal state, both the tabletop 14 and the radiation imaging unit 15 are locked so as not to move. When the tabletop 14 is moved from this state, the radiologist steps on the foot switch 44. Then, the controller 43 releases the locking mechanisms 41 and 42 of both directions and disengages the connection to the clutch 46 so as to allow the driving pulley 47 to freely rotate. Thus, the tabletop 14 can freely move. The radiologist fixes the tabletop 14 by releasing the foot switch 44 at a desired position.

On the other hand, while the tabletop 14 is being moved, the imaging unit locking mechanism 52 maintains a locking state. Then, in accordance with the movement of the tabletop 14, the roller 34 that supports the radiation imaging unit 15 rotates within the second slot 28b of the frame 25. Accordingly, the radiation imaging unit 15 maintains a relative position in relation to the base unit 12 without interlocking with the movement of the tabletop 14.

By the aligning method that moves only the tabletop 14, the photographing operation can be effectively performed because the positional relationship between the radiation imaging unit 15 and the X-ray tube 18 is fixed. On the other hand, when the patient P should not be moved, or there is an obstacle such as an instrument attendant to the patient P around the apparatus, the radiation imaging unit 15 and the X-ray tube 18 are moved to the portion of the patient P to be photographed so as to perform the photographing operation.

In the horizontal movement member 19 attached to the ceiling, a position sensor 55 is provided that detects the moving position in the lengthwise direction. When the alignment is performed by moving the X-ray tube 18, the radiologist releases only the lock of the tube supporting mechanism 17 in the widthwise direction. Then, the radiologist moves the X-ray tube 18 in the widthwise direction, and again locks the tube supporting mechanism 17 at a desired position. The movement is detected by the position sensor 55, and when there is a difference between the outputs from the position sensors 55 and 53, the controller 43 performs control so that the outputs match with each other.

That is, after the locking by the imaging unit locking mechanism 52 is released, the controller 43 moves the radiation imaging unit 15 by controlling the drive unit 45. Then, the controller 43 stops the drive unit 45 at the position where both outputs match with each other, namely, at the position where the positions of the X-ray tube 18 and the radiation imaging unit 15 in the lengthwise direction match with each other. Then, the imaging unit locking mechanism 52 fixes the radiation imaging unit 15.

On the contrary, the alignment can also be performed in such a manner that the controller 43 moves the radiation imaging unit 15, and then the X-ray tube 18 is aligned to the position to which the radiation imaging unit 15 is moved. In this case, an operation unit for instructing the movement of the radiation imaging unit 15 is provided in the tabletop frame so that the radiologist operates a switch to give a moving direction and to place the radiation imaging unit 15 at the desired position. After that, the position of the X-ray tube 18 is automatically or manually aligned with the radiation imaging unit 15.

Third Embodiment

Figure 6:
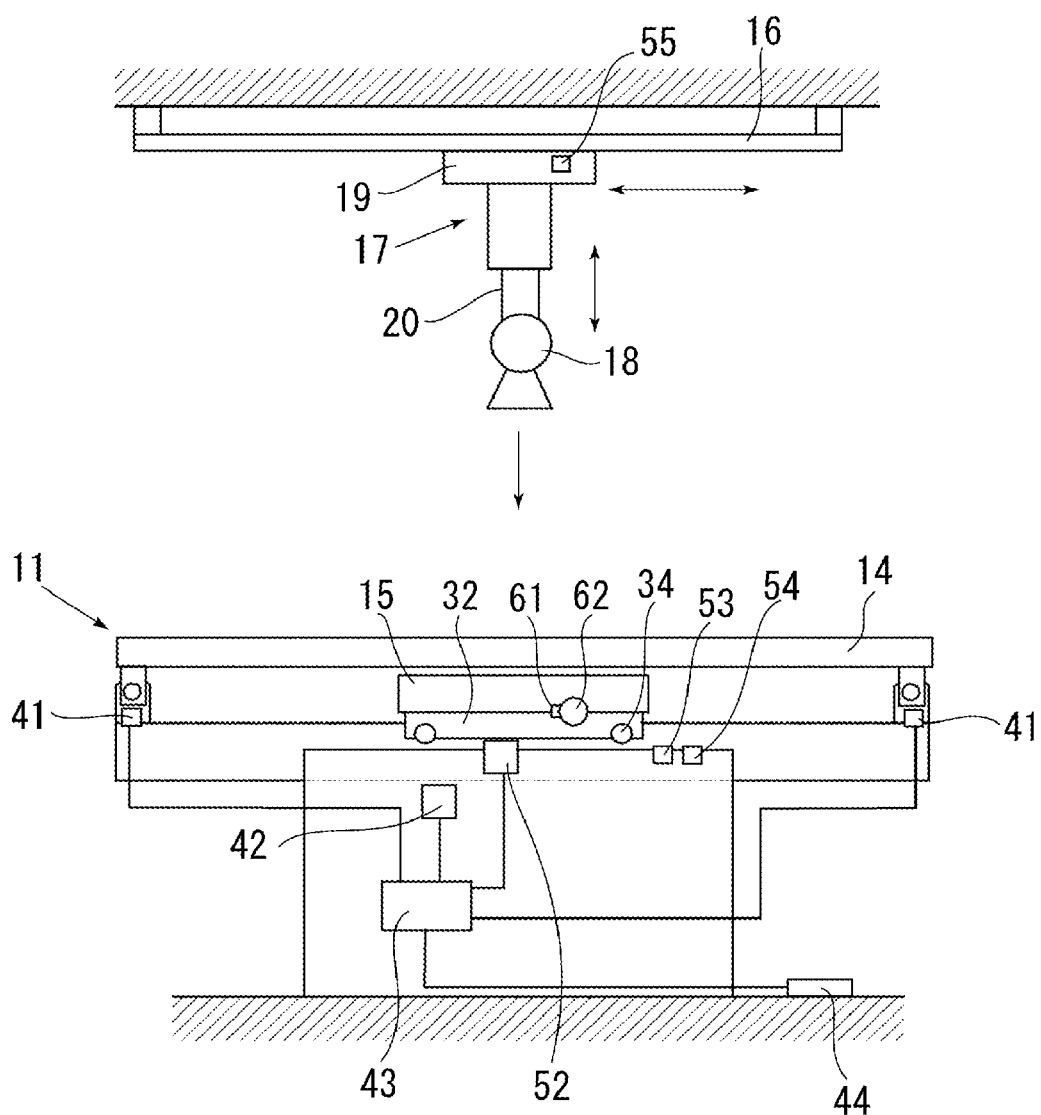
FIG. 6 is a diagram that illustrates the radiation imaging apparatus according to a third embodiment of the present invention.

FIG. 6 is a diagram that illustrates a third embodiment of the present invention, in which the movement of the radiation imaging unit 15 is performed manually. The components that are provided with the same numerals and symbols as the example shown in FIG. 5 have the same function as in FIG. 5, and accordingly, the explanation thereof is not repeated. In the third embodiment, the drive unit 45, driven pulleys 48 and 49, and the timing belt 50 are unnecessary, and a switch 61 for releasing the imaging unit locking mechanism 52 and a handle 62 for moving the radiation imaging unit 15 are provided. The switch 61 is turned on when the radiologist grips a circumference of the moving handle 62. Accordingly, the lock can be released without pressing the switch 61 by the radiologist at the time of moving, and thus a good operability can be achieved.

Upon detection of a signal indicating that the switch 61 is turned on, the controller 43 releases the locking of the imaging unit locking mechanism 52. Thus, the radiation imaging unit 15 is in a movable state. The radiologist moves the radiation imaging unit 15 using the handle 62, and again locks the radiation imaging unit 15 by releasing the handle 62.

Fourth Embodiment

Figure 7:
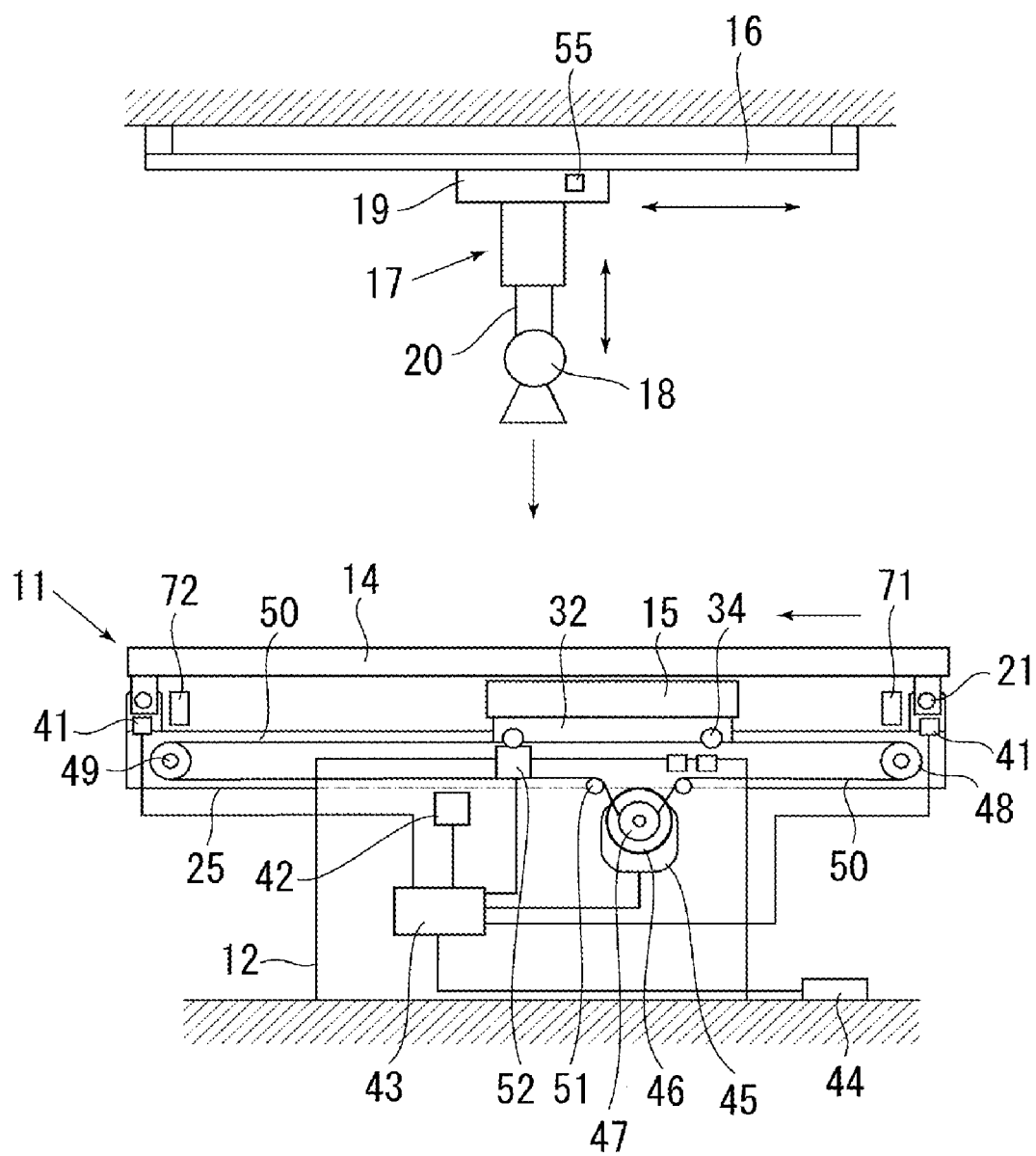
FIG. 7 is a diagram that illustrates the radiation imaging apparatus according to a fourth embodiment of the present invention.

The table according to a fourth embodiment of the present invention as shown in FIG. 7 has a structure for previously avoiding a collision, in addition to the configuration of the second embodiment. Close-contact detection devices 71 and 72 are provided in a proximity of the frame members 25c and 25d of the frame 25. The close-contact detection devices 71 and 72 are not in interlock with the movement of the tabletop 14 in the widthwise direction, but is in interlock with the movement of the tabletop 14 in the lengthwise direction. The close-contact detection devices 71 and 72 detect the close contact when the distance between the tabletop 14 and the radiation imaging unit 15 in the lengthwise direction is below a prescribed value.

For example, in a state in which the radiation imaging unit 15 is disposed at a rightward position, if the tabletop 14 is manually moved carelessly in a large amount to the left indicated by an arrow as shown in FIG. 7, the widthwise movement mechanism 21 can collide with the radiation imaging unit 15. The tabletop 14 usually weighs thirty to forty kilograms, and if the patient P weighing seventy kilograms is placed onto the tabletop 14, the total weight exceeds one hundred kilograms. Thus, the impact when the collision occurs is high even if the speed of moving is low. In a worst case, there is a danger that the radiation imaging unit 15 is broken or goes out of order.

In this regard, the close-contact detection device 71 detects the close contact of the tabletop 14 that moves to the left, with the radiation imaging unit 15. The signal sent from the close-contact detection device 71 is inputted to the controller 43 together with the signals from the foot switch 44 and the handle 62. Then, in accordance with the result of detection by the close-contact detection device 71, an input operation by the foot switch 44 and the handle 62 is restricted.

More specifically, an operator releases the lock of the tabletop 14 by the foot switch 44, and then the close contact is detected by the close-contact detection device 71 while the operator moves the tabletop 14 to the left. Then, the controller 43 releases the lock of the radiation imaging unit 15. The controller 43 performs control so that the radiation imaging unit 15 moves to the left along with the movement of the tabletop 14. Alternatively, the controller 43 can control the locking mechanism 42 so that the movement of the tabletop 14 is stopped. The control procedure is previously set to the controller 43 by the instruction of the radiologist according to usage pattern of the apparatus.

Fifth Embodiment

Figure 8:
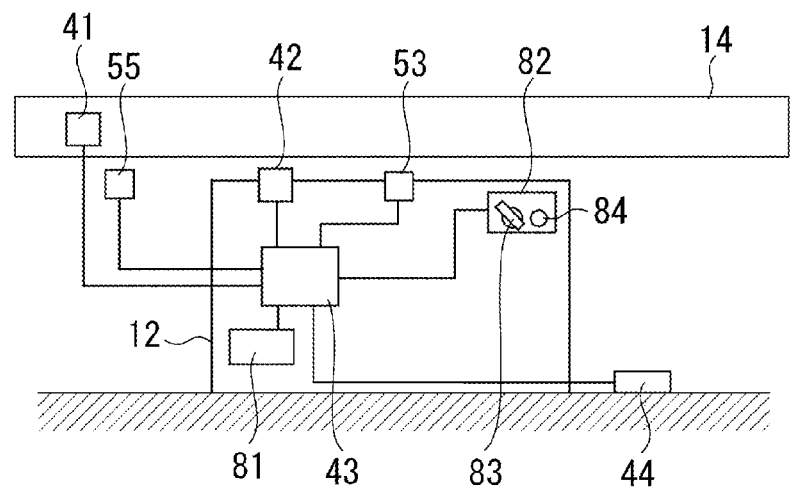
FIG. 8 is a diagram that illustrates the radiation imaging apparatus according to a fifth embodiment of the present invention.

FIG. 8 is a diagram that illustrates the configuration of a fifth embodiment of the present invention by which the moving range of the tabletop 14 can be set. Inside the base unit 12, the controller 43 and a storage unit 81 are provided. The controller 43 controls the lengthwise locking mechanism 42 and the widthwise locking mechanism 41 of the tabletop 14. The storage unit 81 has a memory for storing a plurality of setting values. An input unit 82 for setting the permissible scope/range of movement by the radiologist is provided. The output from the input unit 82 is connected to the controller 43. The input unit 82 is provided with a switching lever 83 and a setting switch 84.

Figure 9A:
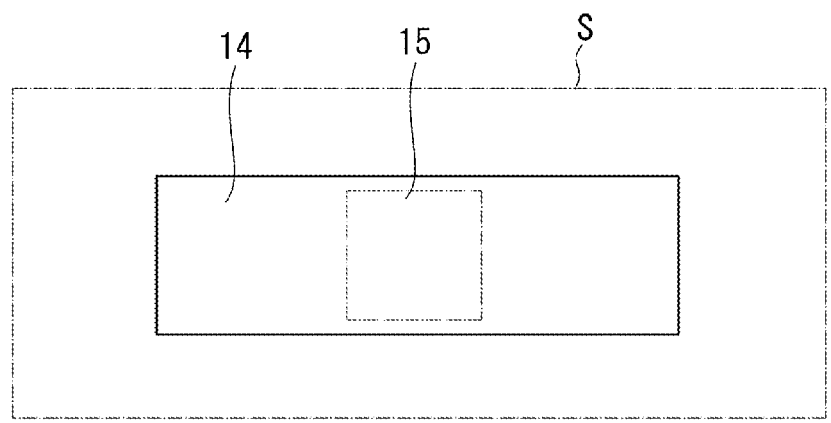
FIG. 9A and FIG. 9B are explanatory diagrams that respectively illustrate a movable scope of the tabletop.
Figure 9B:
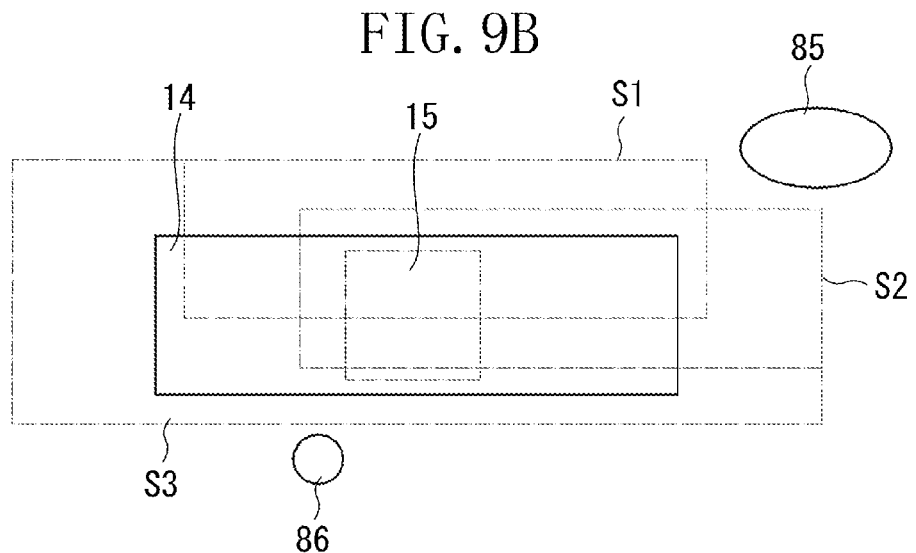
Figure 10:
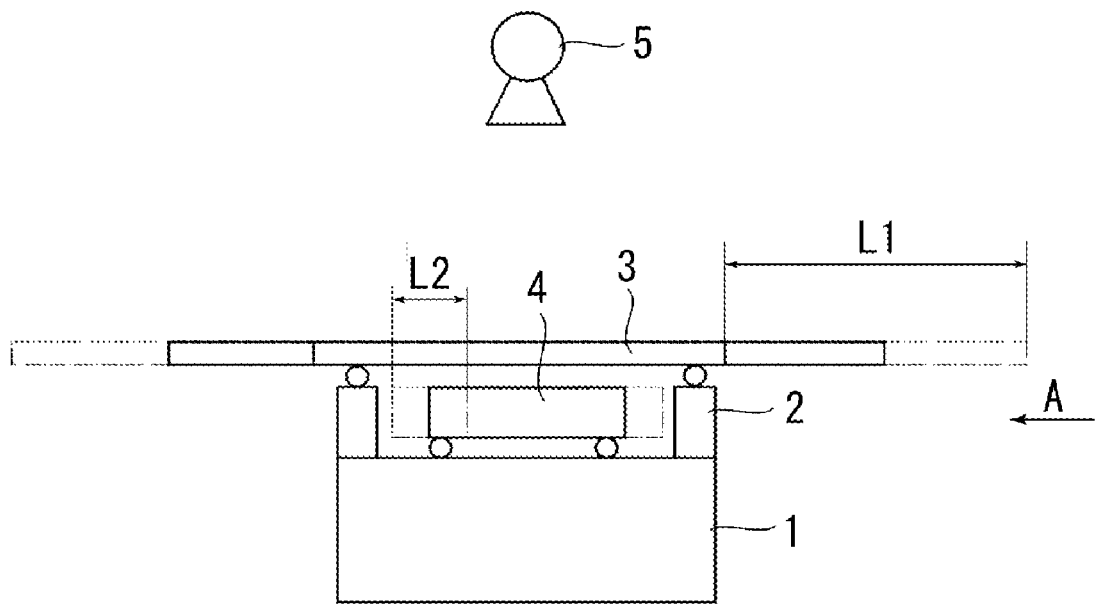
FIG. 10 is a diagram that illustrates a configuration of a conventional example.

FIGS. 9A and 9B are explanatory diagrams that respectively illustrate the table seen from above according to the fifth embodiment of the present invention. The tabletop 14 is capable of freely moving within a scope S, as shown in FIG. 9A. However, when an appliance 85 such as a monitor and an appliance 86 such as a drip infusion stand attendant to the patient, are placed around the apparatus as shown in FIG. 9B, the moving scope of the tabletop 14 is restricted. In such a case, by previously setting the moving scope of the tabletop 14, the collision of the tabletop 14 with the appliances 85 and 86 can be avoided.

As shown in FIG. 9B, in the case where the appliances 85 and 86 are placed around the patient, first, the radiologist operates the switching lever 83, and sets the imaging table to be in a state in which positional information of movable scope of the tabletop 14 is inputted. Then, the radiologist moves the tabletop 14 to close positions S1 and S2 at which the tabletop 14 does not collide with the appliance 85. When the tabletop 14 is moved to the positions S1 and S2, the radiologist presses the setting switch 84. Then, the controller 43 detects the pressing operation of the setting switch 84. Then, the controller 43 obtains the values of the position sensor 53 and the position sensor 55 at the time of the detection, and stores the values in the storage unit 81. In the same way, the radiologist moves the tabletop 14 to a position S3 to which the tabletop 14 is movable in relation to the appliance 86, then presses the setting switch 84 to obtain the positional information, and stores the positional information in the storage unit 81.

After setting of the moving scope of the tabletop 14 is completed, the radiologist returns the switching lever 83 to the initial position. Upon detection of the operation, the controller 43 computes coordinates of the movable position based on the stored positional information, so that the setting as to the moving scope is effective. The radiologist moves the tabletop 14 by operating the foot switch 44. When the values of the position sensors 53 and 55 match the threshold coordinates of the movable position, the controller 43 locks the tabletop 14. By separately and independently controlling the widthwise locking mechanism 41 and the lengthwise locking mechanism 42, the moving can be performed only within the scopes S1, S2, and S3 as shown in FIG. 9B, which are indicated by alternate long and short dashed lines.

Alternatively, the controller 43 is also capable of setting the moving scope of the tabletop 14 in plural different patterns. For example, in FIG. 9B, suppose that the appliance 85 is always placed beside the table and the appliance 86 is temporarily placed. In this case, the setting is performed so that the switching lever 83 can switch between plural settings. For example, if according to a setting A, only the collision with the appliance 85 is avoided, and according to a setting B, the collision with both the appliances 85 and 86 is avoided, the table according to this embodiment can be flexibly used. The control procedure for these settings can be implemented in such a manner that the controller 43 obtains the positional information from the storage unit 81 so as to compute the coordinates of the movable position.

Further, in addition to the restriction on movement in the horizontal direction, the restriction on the vertical movement of the tabletop 14 can be added. That is, in a case where the appliances 85 and 86 are placed below the tabletop 14 and there is a danger of collision with the descending tabletop 14, a lowermost position to which the tabletop 14 can be descended, can be previously stored so as to set the moving scope.

In the above embodiment, the X-ray detection device is used as an example for the radiation imaging unit 15, however, the same effect can be achieved by using the cassette that stores the film or the stimulable phosphor sheet for the X-ray image-receiving unit of the radiation imaging unit 15.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2005-301275 filed Oct. 17, 2005, which is hereby incorporated by reference herein in its entirety.

What is claimed is:

1. A radiation imaging apparatus comprising:
   a tabletop onto which a patient lays down;
   a radiation imaging unit positioned below the tabletop and configured to detect radiation that transmits through the patient;
   a moving mechanism unit including a lengthwise moving mechanism configured to move the moving mechanism unit in a lengthwise direction, the moving mechanism unit supporting the radiation imaging unit which is movable in the lengthwise direction;
   a base unit supporting the moving mechanism unit;
   a sensor configured to detect a relative position of the radiation imaging unit with respect to the tabletop in the lengthwise direction; and
   a controller controlling the movement of the radiation imaging unit based on detection by the sensor.

2. The radiation imaging apparatus according to claim 1, further comprising a widthwise moving member supporting the tabletop and configured to move the tabletop in a widthwise direction, wherein the widthwise moving member is disposed on both ends of the tabletop in the lengthwise direction.

3. The radiation imaging apparatus according to claim 1, further comprising a locking mechanism configured to switch to a noninterlocked state in which a position of the radiation imaging unit before moving is maintained in relation to the base unit without interlocking with movement of the tabletop.

4. The radiation imaging apparatus according to claim 1, further comprising:
   a close-contact detection device provided in the moving mechanism unit in the lengthwise direction and configured to detect whether the tabletop and the radiation imaging unit are brought into close contact with each other.

* * * * *